(12) United States Patent
Edelberg et al.

(10) Patent No.: US 7,910,694 B2
(45) Date of Patent: Mar. 22, 2011

(54) HOMING PEPTIDES TO RECEPTORS OF HEART VASCULATURE

(75) Inventors: Jay M. Edelberg, New York, NY (US);
Dong Qing Cai, Guangzhou (CN);
Barbara L. Hempstead, New York, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 1364 days.

(21) Appl. No.: 10/527,832

(22) PCT Filed: Sep. 18, 2003

(86) PCT No.: PCT/US03/29379
§ 371 (c)(1),
(2), (4) Date: Sep. 19, 2005

(87) PCT Pub. No.: WO2004/026327
PCT Pub. Date: Apr. 1, 2004

(65) Prior Publication Data
US 2006/0149034 A1    Jul. 6, 2006

Related U.S. Application Data

(60) Provisional application No. 60/412,330, filed on Sep. 19, 2002.

(51) Int. Cl.
*A61K 38/04*    (2006.01)
*A61K 38/00*    (2006.01)
*A61K 51/00*    (2006.01)

(52) U.S. Cl. ......... 530/329; 530/300; 530/324; 514/1.1; 424/1.69

(58) Field of Classification Search .................. None
See application file for complete search history.

*Primary Examiner* — Maury Audet
(74) *Attorney, Agent, or Firm* — Hoffmann & Baron, LLP

(57) ABSTRACT

The present invention relates to peptides which selectively or preferentially home to areas of a heart. The invention further relates to conjugates of the homing peptides and uses thereof.

4 Claims, 12 Drawing Sheets

Figure 1

```
  1  RTPSDKPVAH VVANPQAEGQ LQWLNRRANA LLANGVELRD NQLVVPSEGL
 51  YLIYSQVLFK GQGCPSTHVL LTHTISRIAV SYQTKVNLLS AIKSPCQRET
101  PEGAEAKPWY EPIYLGGVFQ LEKGDRLSAE INRPDYLLFA ESGQVYFGII
151  AL          (SEQ ID NO: 6)
```

Figure 2

```
  1  HSDPARRGQL SVCDSISEWV TAADKKTAVD MSGGTVTVLE KVPVSKGQLK
 51  QYFYETKCNP MGYTKEGCRG IDKRHWNSQC RTTQSYVRAL TMDSKKRIGW
101  RFIRIDTSCV CTLTIKRGR
                         (SEQ ID NO: 7)
```

HOMING PEPTIDES TO RECEPTORS OF HEART VASCULATURE

This application is a U.S. National Phase Application of International Application No. PCT/US2003/029379 filed on Sep. 18, 2003. The specification of International Application No. PCT/US2003/029379 is hereby incorporated by reference.

This application asserts priority to U.S. Provisional Application Ser. No. 60/412,330 filed on Sep. 19, 2002. The specification of U.S. Provisional Application Ser. No. 60/412,330 is hereby incorporated by reference.

The invention described in this application was made with finds from the National Institutes of Health, Grant Number R01 AG20918-01. The United States government has certain rights in the application.

BACKGROUND OF THE INVENTION

The vasculature of a heart is comprised of blood vessels, such as arteries and veins, and the microvasculature. The microvasculature includes capillaries, arterioles, and venules, and are comprised of microvasculature endothelial cells. Numerous receptors are present on the cells that constitute the vasculature of a heart. The receptors known to exist on the cells include tumor necrosis factor (TNF) receptors and brain derived neurotrophic factor (BDNF) receptors.

Disease of the heart vasculature, i.e., cardiovascular disease, is the leading cause of morbidity and mortality in older individuals. As the populations ages, the need for optimal geriatric therapies is an increasingly important public health issue. Currently, myocardial infarction in older individuals has a significantly worse prognosis with higher mortality and complication rates than younger individuals. Furthermore, depending, in part, on the extent of vascular damage, an individual can have areas of the heart which are "old" (i.e., relatively unhealthy) and other areas which are "young" (i.e., relatively healthy). Therefore, senescent changes in the cardiovascular system plays an important role in predisposing older areas of the heart or older hearts, to increased vascular pathology.

Therefore, there is a need to determine the condition of a heart and to provide treatments targeted to specific areas of a heart.

SUMMARY OF THE INVENTION

In one aspect, the invention relates to an isolated peptide comprising or consisting of the amino acid sequence QA(Q/E)GQLV (SEQ. ID. NO: 1). The peptide selectively homes to TNF receptor(s) in the vasculature of a heart.

In another embodiment, the invention relates to an isolated peptide comprising or consisting of the amino acid sequence ARRGQAV (SEQ. ID. NO: 4). The peptide preferentially homes to BDNF receptor(s) in the vasculature of a heart.

In another embodiment, the invention relates to an isolated peptide comprising or consisting of the amino acid sequence G(R/W)RFIRV (SEQ. ID. NO: 2). The peptide preferentially homes to BDNF receptor(s) in the vasculature of a heart.

In another embodiment, the invention relates to a conjugate comprising a peptide which comprises or consists of the amino acid sequence QA(Q/E)GQLV (SEQ. ID. NO: 1) or functionally equivalent modifications thereof, and a functional moiety. The peptide selectively homes to TNF receptor(s) in the vasculature of a heart.

In another embodiment, the invention relates to a conjugate comprising a peptide which comprises or consists of the amino acid sequence ARRGQAV (SEQ. ID. NO: 4) or functionally equivalent modifications thereof, and a functional moiety. The peptide preferentially homes to BDNF receptor(s) in the vasculature of a heart.

In another embodiment, the invention relates to a conjugate comprising a peptide which comprises or consists of the amino acid sequence G(R/W)RFIRV (SEQ. ID. NO: 2) or functionally equivalent modifications thereof, and a functional moiety. The peptide preferentially homes to BDNF receptor(s) in the vasculature of a heart.

In another embodiment, the invention relates to a method for determining a young heart or young areas of a heart vasculature in a mammal. The method comprises administering to the mammal a peptide comprising or consisting of the amino acid sequence QA(Q/E)GQLV (SEQ. ID. NO: 1) or functionally equivalent modifications thereof, conjugated to a detectable marker, wherein the peptide selectively homes to TNF receptor(s) in the vasculature of the heart and the marker is detected. A disproportionately high binding of the peptide comprising or consisting of QA(Q/E)GQLV (SEQ. ID. NO: 1) indicates a young heart or young areas of a heart vasculature.

In another embodiment, the invention relates to a method for determining an old heart or old areas of a heart vasculature in a mammal. The method comprises administering to the mammal a peptide comprising or consisting of the amino acid sequence ARRGQAV (SEQ. ID. NO: 4) or G(R/W)RFIRV (SEQ. ID. NO: 2) or functionally equivalent modifications thereof, conjugated to a detectable marker, wherein the peptide selectively homes to BDNF receptor(s) in the vasculature of the heart and the marker is detected. A disproportionately high binding of the peptide comprising or consisting of ARRGQAV (SEQ. ID. NO: 4) or G(R/W)RFIRV (SEQ. ID. NO: 2) indicates an old heart or old areas of a heart vasculature.

In another embodiment, the invention relates to a method for determining the condition of the vasculature of a heart in a mammal. The method comprises administering to the mammal a first peptide comprising or consisting of the amino acid sequence QA(Q/E)GQLV (SEQ. ID. NO: 1) or functionally equivalent modifications thereof, conjugated to a first detectable marker. The first peptide selectively homes to TNF receptor(s) in the vasculature of the heart. The method further comprises administering to the mammal a second peptide comprising or consisting of the amino acid sequence ARRGQAV (SEQ. ID. NO: 4) or G(R/W)RFIRV (SEQ. ID. NO: 2) or functionally equivalent modifications thereof, conjugated to a second detectable marker. The second peptide homes to BDNF receptor(s) in the vasculature of the heart. The first and second marker are detected. A disproportionately high ratio of binding of the first peptide to the second peptide indicates a young heart or young areas of the heart vasculature. Alternatively, a disproportionately low ratio of binding of the first peptide to the second peptide indicates an old heart or old areas of the heart vasculature.

In another embodiment, the invention relates to a method for delivering a functional moiety selectively to a young heart or a young area of the heart in a mammal. The method comprises administering to the mammal a conjugate comprising a peptide which comprises or consists of the amino acid sequence QA(Q/E)GQLV (SEQ. ID. NO: 1) or functionally equivalent modifications thereof, and a functional moiety.

In another embodiment, the invention relates to a method for delivering a functional moiety preferentially to an old heart or an old area of the heart in a mammal. The method comprises administering to the mammal a conjugate comprising a peptide which comprises the amino acid sequence ARRGQAV (SEQ. ID. NO: 4) or G(R/W)RFIRV (SEQ. ID. NO: 2) or functionally equivalent modifications thereof, and a functional moiety.

In another embodiment, the invention relates to a method for discovering mimics of peptides comprising or consisting of amino acid sequence QA(Q/E)GQLV (SEQ. ID. NO: 1) or functionally equivalent modifications thereof. The method comprises determining a three-dimensional structure of peptides comprising or consisting of the sequence; identifying compounds comprising the structure; and determining the capacity of the compounds for selective homing to TNF receptor(s) in the vasculature of a heart. The compounds which home selectively to TNF receptor(s) in the vasculature of the heart are mimics.

In another embodiment, the invention relates to a method for discovering mimics of peptides comprising or consisting of amino acid sequence ARRGQAV (SEQ. ID. NO; 4) or G(R/W)RFIRV (SEQ. ID. NO: 2) or functionally equivalent modifications thereof. The method comprises determining a three-dimensional structure of peptides comprising or consisting of the sequence; identifying compounds comprising the structure; and determining the capacity of the compound for homing to BDNF receptor(s) in a vasculature of a heart. The compounds which home preferentially to BDNF receptor(s) in the vasculature of the heart are mimics.

BRIEF DESCRIPTION OF THE FIGURES

FIG. 1. Amino acid sequence of human TNFα Genbank Accession No. 1TNFA (SEQ. ID. NO: 6).

FIG. 2. Amino acid sequence of human BDNF Genbank Accession No. 1BNDA (SEQ. ID. NO: 7).

DETAILED DESCRIPTION OF THE INVENTION

Figure 3:
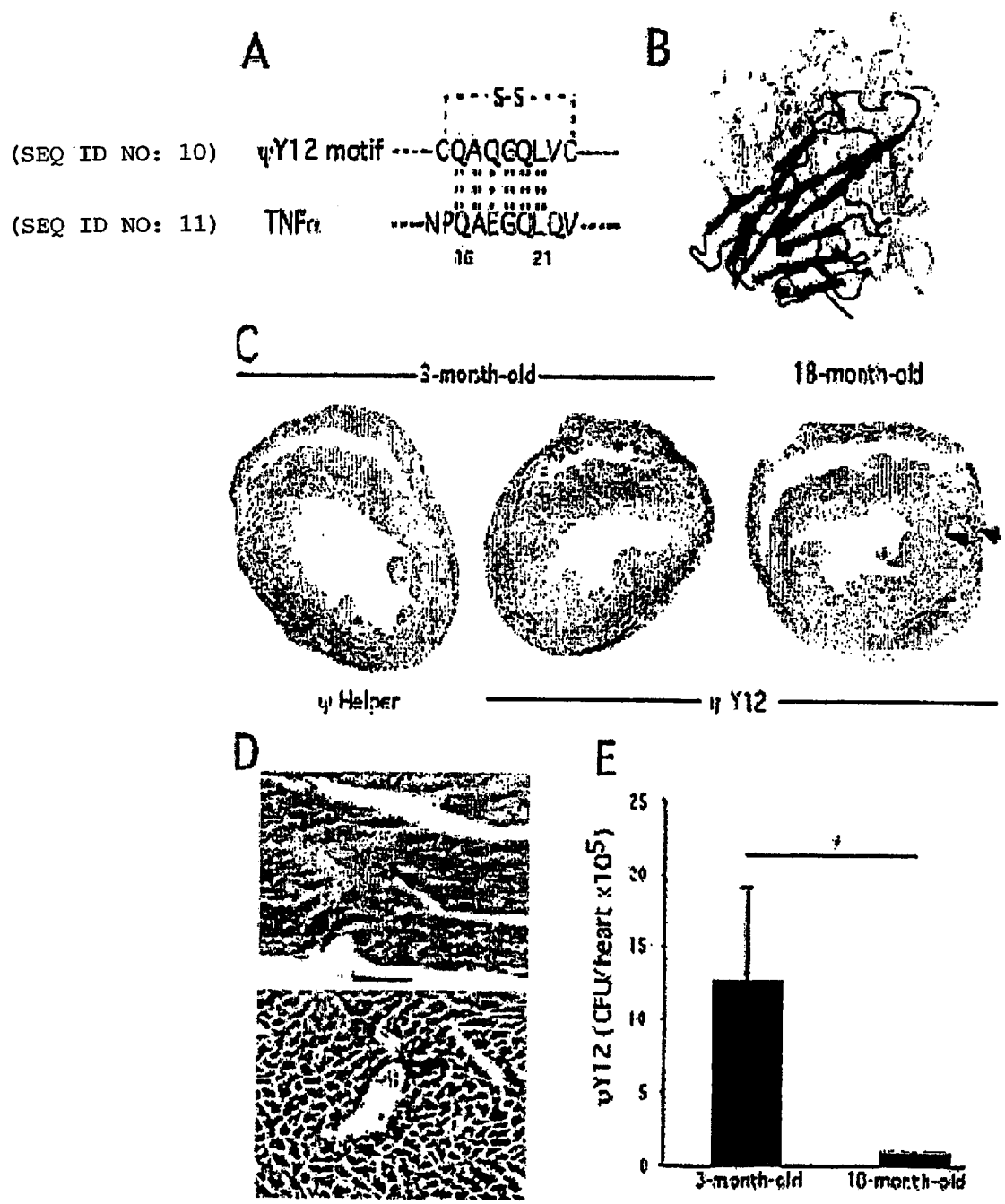
FIG. 3. Identification of aging-associated changes in cardiac microvascular epitope binding. (A) ψY12 epitope sequence homology to TNFα. (B) Homologous region is highlighted yellow in the three-dimensional structure of TNFα. (C) Representative phage immunostaining patterns in hearts with isolated helper phage and ψY12 clones with minimal labeling of the 18-month old hearts (arrows). (D) ψY12 phage binding the cardiac microvasculature of 3-month old hearts (arrow). (E) ψY12 phage titers of 3- and 18-month old hearts.

The invention is based on the surprising discovery that a peptide having the amino acid sequence QAQGQLV (SEQ. ID. NO: 3) binds to receptors in the heart vasculature in a mammal, but does not bind significantly to receptors on other organs. Similarly, a peptide having the amino acid sequence ARRGQAV (SEQ. ID. NO: 4) or GRRFIRV (SEQ. ID. NO: 5) binds to receptors in the vasculature of the heart and brain, but do not bind significantly to receptors on other organs.

Also surprisingly, a peptide having the amino acid sequence QAQGQLV (SEQ. ID. NO: 3) binds with more binding capacity to TNF receptor(s) in the vasculature of hearts which are "young" (i.e., healthy) than to TNF receptor(s) in the vasculature of older hearts (i.e., unhealthy). Another discovery is that young hearts have more TNF receptor 1 present than do older hearts. The inventors also surprisingly discovered that treatment of myocardial infarction with TNFα markedly reduced the extent of myocardial infarction in young hearts, but induced apoptosis of cardiac cells in older hearts.

Furthermore, the inventors also discovered that a peptide having the amino acid sequence ARRGQAV (SEQ. ID. NO: 4) or GRRFIRV (SEQ. ID. NO: 5) bind to BDNF receptor(s) in the vasculature of older hearts, usually to trkB receptors, and more commonly to truncated trkB receptors. Another discovery is that older hearts have more truncated trkB receptors than do younger hearts. The inventors also surprisingly discovered that treatment of myocardial infarction with BDNF had no effect on myocardial infarctions in young hearts. In older hearts, BDNF increased the extent of myocardial infarction, induced inflammatory infiltration, and aneurysm formation.

As a result of the surprising discoveries described above, the present invention provides isolated peptides which selectively or preferentially home to TNF receptor(s) or BDNF receptor(s) in the vasculature of a heart. Preferably, the homing peptides of the present invention bind to receptors of the microvasculature of a heart, especially on microvasculature endothelial cells.

In one embodiment, a homing peptide comprises the amino acid sequence QA(Q/E)GQLV (SEQ. ID. NO: 1) or a functionally equivalent modification thereof. The amino acid sequence QA(Q/E)GQLV (SEQ. ID. NO: 3) is homologous to a sequence found at amino acid positions 16-22 of human TNFα (FIG. 1). If the homing peptide comprises the amino acid sequence QAQGQLV (SEQ. ID. NO: 3), the amino acid residues at positions 1-2 and 4-6 are identical to the amino acid residues found at positions 16-17 and 19-21 of human TNFα. If the homing peptide comprises the amino acid sequence QAEGQLV (SEQ. ID. NO: 8), the amino acid residues at positions 1-6 are identical to the amino acid residues found at positions 16-20 of human TNFα.

Homing peptides comprising the amino acid sequence QA(Q/E)GQLV (SEQ. ID. NO: 1) selectively home to TNF receptor(s) in the vasculature of a heart.

The TNF receptor(s) can be any receptor which binds TNFα. Examples of TNF receptors include TNF receptor (TNFR) 1, TNFR2 (i.e., p75), and receptors which are homologous to TNRF 1 or TNFR2, such as receptors in the TNFR superfamily. Preferably, the TNF receptor is TNFR1.

In another embodiment, a homing peptide comprises the amino acid sequence ARRGQAV (SEQ. ID. NO: 4) or G(R/W)RFIRV (SEQ. ID. NO: 2), or a functionally equivalent modification thereof.

The amino acid sequence ARRGQAV (SEQ. ID. NO: 4) is homologous to a sequence found at amino acid positions 5-11 of human BDNF (FIG. 2). The amino acid residues at positions 1-5 of amino acid sequence ARRGQAV (SEQ. ID. NO: 4) are identical to the amino acids at positions 5-9 of human BDNF (FIG. 2).

The amino acid sequence G(R/W)RFIRV (SEQ. ID. NO: 2) is homologous to a sequence found at amino acid positions 99-105 of human BDNF. If the homing peptide comprises the amino acid sequence GRRFIRV (SEQ. ID. NO: 5), the amino acid residues at positions 1 and 3-6 are identical to the amino acid residues found at positions 99 and 101-104 of human BDNF (FIG. 2). If the homing peptide comprises GWRFIRV (SEQ. ID. NO: 9), the amino acid residues at positions 1-6 are identical to the amino acid residues found at positions 99-104 of human BDNF.

Homing peptides comprising the amino acid sequence ARRGQAV (SEQ. ID. NO: 4) or G(R/W)RFIRV (SEQ. ID. NO: 2) preferentially home to BDNF receptor(s) in the vasculature of a heart.

The BDNF receptor(s) can be any receptor which binds BDNF. Examples of BDNF receptors include, trkB, p75, and the nerve growth factor family of receptors, such as trkA and trkc. Usually, the BDNF receptor is trkB, and more commonly truncated trkB. "Truncated trkB" as used herein means that the trkB receptor lacks the intracellular tyrosine kinase domain. For example, the trkB receptor can lack the entire intracellular tyrosine kinase domain or can lack a portion of the domain. Typically, the truncated trkB receptor lacks a portion of the domain sufficient to cause loss of kinase activity.

The term "peptide" as used herein means an amino acid sequence having at least five amino acid residues. No distinction will be made between a peptide, polypeptide, or protein. The peptide of the invention can be linear, cyclic, or branched.

The peptides of the invention include functionally equivalent modifications of SEQ. ID. NOs: 1, 2, 3, 4, 5, 8 and 9. A functionally equivalent modification refers to a molecule having a similar, non-identical sequence and the selective or preferential homing property described herein. A functionally equivalent modification can be, for example, two, preferably one deletions and/or substitutions relative to the reference peptide sequence. Any deletions or substitutions in the amino acid sequence of the reference peptide are permitted provided that the peptide of the invention continues to satisfy the functional criteria described above and below.

Substitutions in the amino acid sequence of the reference peptide are preferably with equivalent amino acids. Groups of amino acids known to be of equivalent character are listed below:
  (a) Ala(A), Ser(S), Thr(T), Pro(P), Gly(G);
  (b) Asn(N), Asp(D), Glu(E), Gln(O);
  (c) His(H), Arg(R), Lys(K);
  (d) Met(M), Leu(L), Ile(I), Val(V); and
  (e) Phe(F), Tyr(Y), Trp(W).

The deletions can include any one or two amino acid residue deletions. Preferably, the deletions are one or two amino acid residues at either the N- or C-terminal of the reference peptide. Most preferably, the deletions are the amino acid residues that are not homologous to TNFα or BDNF.

Therefore, in this specification, when reference is made to amino acid sequences QA(Q/E)GQLV (SEQ. ID. NO: 1), ARRGQAV (SEQ. ID. NO: 4), or G(R/W)RFIRV (SEQ. ID. NO: 2), the functionally equivalent modifications are also included.

Preferred amino acid residues for the functionally equivalent modifications of the peptide comprising the amino acid sequence QA(Q/E)GQLV (SEQ. ID. NO: 1) are a Q at amino acid position 3 or a V at amino acid position 7. In an especially preferred embodiment, Q is present at amino acid position 3 and V is present at amino acid position 7.

Similarly, preferred amino acid residues for the functionally equivalent modifications of the peptide comprising the amino acid sequence ARRGQAV (SEQ. ID. NO: 4) are an A at amino acid position 6 or a V at amino acid position 7. In an especially preferred embodiment, A is present at amino acid position 6 and V is present at amino acid position 7.

Likewise, preferred amino acid residues for the functionally equivalent modifications of the peptide comprising the amino acid sequence G(R/W)RFIRV (SEQ. ID. NO: 2) are a W at amino acid position 2 or a V at amino acid position 7. In an especially preferred embodiment, W is at amino acid position 2 and V is at amino acid position 7.

The homing peptides described above can further comprise additional amino acid residues. The additional amino acids residues can be any number such that the peptide selectively or preferentially homes to the receptor(s) described above in the vasculature of a heart. For instance, the homing peptide can be a relatively short peptide. The approximate minimum number of amino acid residues in the peptide can, for example, be 5, 7, 10, 15, 20, 30, or 40 amino acids in length. There is no particular maximum number of amino acid residues for the homing peptides of the peptide invention. For example, a suitable maximum number of amino acid residues in the peptide can be approximately 200, more preferably approximately 175, and even more preferably approximately 150 amino acid residues.

The additional amino acid residues can be any amino acid residue such that the peptide selectively or preferentially homes to the receptor(s) described above in the vasculature of a heart. For example, if the homing peptide comprises the amino acid sequence QA(Q/E)GQLV (SEQ. ID. NO: 1), the additional amino acid residues can be any one or more amino acid residues that occur naturally at the N-terminal and/or C-terminal side of amino acid residues at positions 16-22 of human TNFα (FIG. 1).

For instance, naturally occurring amino acid resides which can be found N-terminal to amino acid residues at positions 16-22 of human TNFα include the amino acid residues approximately at positions 10-15, 5-15, and 2-15 of human TNFα. Similarly, naturally occurring amino acid resides which can be found C-terminal to amino acid residues at positions 16-22 of human TNFα include the amino acid residues approximately at positions 23-60, 23-120, and 23-150 of human TNFα.

Amino acid residues approximately at positions 10-15, 5-15, and 2-15 of human TNFα are preferably attached to the N-terminus of QA(Q/E)GQLV (SEQ. ID. NO: 1). The amino acid residues approximately at positions 23-60, 23-120, and 23-150 are preferably attached to the C-terminus of QA(Q/E)GQLV (SEQ. ID. NO: 1). It is not necessary to have additional amino acid residues at either or at both the N- and C-terminus of QA(Q/E)GQLV (SEQ. ID. NO: 1). For example, the additional amino acid residues can be attached just at the N-terminus of QA(Q/E)GQLV (SEQ. ID. NO: 1) or just at the C-terminus, or both. In addition, the homing peptide can have no additional amino acid residues attached. Thus, the homing peptide can consist of the amino acid sequence QAQGQLV (SEQ. ID. NO: 3) or QAEGQLV (SEQ. ID. NO: 8).

If the homing peptide comprises the amino acid sequence ARRGQAV (SEQ. ID. NO: 4), the additional amino acid residues can be any one or more amino acid residues that occur naturally at the N-terminal and/or C-terminal side of amino acid residues at positions 5-11 of human BDNF (FIG. 2). For example, naturally occurring amino acid resides which can be found N-terminal to amino acid residues at positions 5-11 of BDNF include the amino acid residues approximately at positions 1-4 and 3-4 of BDNF. Similarly, naturally occurring amino acid resides which can be found C-terminal to amino acid residues at positions 5-11 of human BDNF include the amino acid residues approximately at positions 12-30, 12-50, 12-70, 12-90, and 12-110 of BDNF.

Amino acid residues approximately at positions 1-4 or 34 of human BDNF are preferably attached to the N-terminus of ARRGQAV (SEQ. ID. NO: 4). The amino acid residues approximately at positions 12-30, 12-50, 12-70, 12-90, or 12-110 are preferably attached to the C-terminus of ARRGQAV (SEQ. ID. NO: 4). It is not necessary to have additional amino acid residues at either or at both the N- and C-terminus of ARRGQAV (SEQ. ID. NO: 4). For example, the additional amino acid residues can be attached just at the N-terminus of ARRGQAV (SEQ. ID. NO: 4) or just at the C-terminus, or both. In addition, the homing peptide can have no additional amino acid residues attached. Thus, the homing peptide can consist of the amino acid sequence ARRGQAV (SEQ. ID. NO: 4).

If the homing peptide comprises the amino acid sequence G(R/W)RFIRV (SEQ. ID. NO: 2), the additional amino acid residues can be any one or more amino acid residues that occur naturally at the N-terminal and/or C-terminal side of amino acid residues at positions 99-105 of human BDNF (FIG. 2). For example, naturally occurring amino acid resides which can be found N-terminal to amino acid residues at positions 99-105 of BDNF include the amino acid residues approximately at positions 80-98, 60-98, 40-98, 20-98, and 4-98 of BDNF. Similarly, naturally occurring amino acid resides which can be found C-terminal to amino acid residues at positions 99-105 of human BDNF include the amino acid residues approximately at positions 106-109, 106-112, and 106-115 of BDNF.

Amino acid residues approximately at positions 80-98, 60-98, 40-98, 20-98, or 4-98 of human BDNF are preferably attached to the N-terminus of G(R/W)RFIRV (SEQ. ID. NO: 2). The amino acid residues approximately at positions 106-109, 106-112, or 106-115 are preferably attached to the C-terminus of G(R/W)RFIRV (SEQ. ID. NO: 2). It is not necessary to have additional amino acid residues at either or at both the N- and C-terminus of G(R/W)RFIRV (SEQ. ID. NO: 2). For example, the additional amino acid residues can be attached just at the N-terminus of G(R/W)RFIRV (SEQ. ID. NO: 2) or just at the C-terminus, or both. In addition, the homing peptide can have no additional amino acid residues attached. Thus, the homing peptide can consist of the amino acid sequence GRRFIRV (SEQ. ID. NO: 5) or GWRFIRV (SEQ. ID. NO: 9).

The peptides of the invention, including the functionally equivalent modified peptides, are isolated. An isolated peptide is substantially free from other biological components, as well as from materials that may be used in preparation, isolation, characterization or purification of peptides. Examples of other biological components include cellular components, culture media or components (including conditioned media and components thereof, including proteins and nucleic acid molecules), affinity binding agents, such as immunoconjugates or antibodies and other serum components. Examples of materials that may be used in preparation, isolation, or purification of proteins include separation media or membranes, such as nitrocellulose, chromatographic matrices, and electrophoretic gel media, including for instance, polyacrylamide and detergents, such as sodium dodecyl sulfate (SDS).

Preferably, the isolated peptide is at least about 25% to about 90% pure, i.e., free from other peptides and nucleic acid molecules. More preferably, the isolated material is at least about 50% to about 90% pure. Optimally, the isolated peptide is at least about 75% to about 90% pure.

Most preferably, the peptides of the invention, including the functionally equivalent modified peptides, are purified. As used herein, the term "purified" means essentially pure as demonstrated by single band purity on electrophoresis in SDS-polyacrylamide gels (SDS PAGE). Preferably, the purified material is at least about 90% to about 99.9% pure. More preferably, the purified material is at least about 95% to about 99.9% pure. Optimally, the purified material is at least about 99% to about 99.9% pure.

Peptides comprising QA(Q/E)GQLV (SEQ. ID. NO: 1) selectively home to TNF receptor(s) in the vasculature of a heart. A homing peptide is selective for TNF receptor(s) in the heart vasculature if the peptide binds disproportionately to TNF receptor(s) in the heart vasculature, i.e., binds at least two-fold greater to TNF receptor(s) in the heart vasculature than to TNF receptor(s) in non-heart vasculature, such as for example, TNF receptor(s) in the vasculature of the brain or kidney. Preferably, the homing peptide binds at least five-fold greater, and more preferably at least ten times greater to TNF receptor(s) in the heart vasculature than to TNF receptor(s) in non-heart vasculature.

Selective homing can be demonstrated by determining if binding of a homing peptide to TNF receptor(s) in the heart vasculature is specific in accordance with the above definition. For example, the amount of a particular homing peptide bound to TNF receptor(s) in the heart vasculature can be compared to the amount of homing peptide which binds to TNF receptor(s) in non-heart vasculatures. Selective homing can also be determined by showing that peptides that home to the TNF receptor(s) in the heart vasculature are enriched in one or more subsequent rounds of in vivo panning.

Peptides comprising ARRGQAV (SEQ. ID. NO: 4) or G(R/W)RFIRV (SEQ. ID. NO: 2) preferentially home to BDNF receptor(s) in the vasculature of a heart. A homing peptide is preferential for BDNF receptor(s) in the heart vasculature if the peptide binds disproportionately to BDNF receptor(s) in the vasculature of the heart or brain, i.e., binds at least two-fold greater to BDNF receptor(s) in the heart or brain vasculature than to BDNF receptor(s) in non-heart or non-brain vasculatures, such as for example, BDNF receptor(s) in the vasculature of the kidney. Preferably, the homing peptide binds at least five-fold greater, and more preferably at least ten times greater to BDNF receptor(s) in the heart or brain vasculature than to BDNF receptor(s) in non-heart or non-brain vasculature. Binding of the peptide to the vasculature of an organ can be determined by, for example, a binding assay.

The peptides of the present invention can be conjugated to a functional moiety. Due to the selective or preferential homing of the peptides of the present invention to TNF receptor(s) or BDNF receptor(s) in the vasculature of a heart, the functional moiety can be delivered to appropriate areas of the vasculature of a heart. The conjugates can be used to determine the quality (health status) of a heart and/or to deliver therapeutic agents to the appropriate areas of a heart.

In one embodiment, the functional moiety is a detectable marker. The marker can be any marker known to those in the art. For example, the marker can be any marker which emits a detectable signal. Examples of markers include radioisotopes, radionuclides, and fluorophores. An example of a fluorophore include radiofluoronated compounds. Examples of radioisotopes include thallium, iodine$^{125}$, and radioopaque contrast agents.

The markers can be detected by any known method in the art. The method for detecting the marker depends on the marker used. For example, if the markers are radiofluoronated compounds, the markers can be detected by Positron Emission Tomography (PET) scan. If the markers are radioisotopes, the marker can be detected with, for example, a gamma camera. The detectable marker generally allows for detection, visualization, or imaging of the vasculature of a heart.

The homing peptides conjugated to markers can be used to determine the condition of a heart. For example, peptides comprising amino acid sequence QA(Q/E)GQLV (SEQ. ID. NO: 1) bind disproportionately to TNF receptor(s) in the vasculature of a young heart or young portions of a heart vasculature. Disproportionate detection of a marker conjugated to a homing peptide comprising the amino acid sequence QA(Q/E)GQLV (SEQ. ID. NO: 1) indicates a young heart or areas of a heart which are young.

Similarly, peptides comprising amino acid sequence ARRGQAV (SEQ. ID. NO: 4) or G(R/W)RFIRV (SEQ. ID. NO: 2) bind disproportionately to BDNF receptor(s) in the vasculature of an old heart or old portions of a heart vasculature. Disproportionate detection of a marker conjugated to a homing peptide comprising the amino acid sequence ARRGQAV (SEQ. ID. NO: 4) and/or G(R/W)RFIRV (SEQ. ID. NO: 2) indicates an old heart or areas of the heart which are old.

The terms "young" and "old" as used in this specification, do not refer necessarily to the age of the individual. Instead "young" and "old" refer to the condition of the vasculature of a heart. A young individual, for example, can have a heart which is "old" or have portions of the heart which are "old." In contrast, an old individual can have a heart which is "young" or have portions of the heart which are "young."

Young hearts or young portions of a heart vasculature are typically healthy. Old heart or old portions of a heart vasculature are typically unhealthy or damaged.

The disproportionate capacity of a heart or portions of a heart vasculature to bind a peptide comprising the amino acid sequence QA(Q/E)GQLV (SEQ. ID. NO: 1) indicates a young heart or young portions of a heart vasculature. The disproportionate capacity of a heart or portions of a heart vasculature to bind a peptide comprising the amino acid sequence ARRGQAV (SEQ. ID. NO: 4) or G(R/W)RFIRV (SEQ. ID. NO: 2) indicates an old heart or old portions of a heart vasculature.

Administration to a mammal of a peptide comprising the amino acid sequence QA(Q/E)GQLV (SEQ. ID. NO:1) conjugated to a detectable marker can be used to determine whether a heart is young or has young areas. Detection of the marker indicates the capacity of the heart or areas of the heart vasculature to bind TNFα. A disproportionately high binding of the peptide comprising amino acid sequence QA(Q/E)GQLV (SEQ. ID. NO:1) is indicative of a young heart or young areas of a heart vasculature. In contrast, a disproportionately low binding indicates an old heart or old areas of a heart vasculature.

To determine an old heart or old areas of a heart, a peptide comprising the amino acid sequence ARRGQAV (SEQ. ID. NO: 4) or G(R/W)RFIRV (SEQ. ID. NO: 2) conjugated to a detectable marker is administered to a mammal. The capacity of the heart or portions of the heart vasculature to bind BDNF can be determined by detecting the marker. A disproportionately high binding of the peptide comprising the amino acid sequence ARRGQAV (SEQ. ID. NO: 4) or G(R/W)RFIRV (SEQ. ID. NO: 2) is indicative of an old heart or old areas of a heart vasculature. In contrast, a disproportionately low binding indicates a young heart or young areas of a heart vasculature.

Optimally, to determine the condition of a heart, a peptide comprising the amino acid sequence QA(Q/E)GQLV (SEQ. ID. NO: 1) conjugated to a detectable marker and a peptide comprising either the amino acid sequence ARRGQAV (SEQ. ID. NO: 4) or G(R/W)RFIRV (SEQ. ID. NO: 2) conjugated to another detectable marker are administered to a mammal. A disproportionately high ratio of binding of the peptide comprising the amino acid sequence QA(Q/E)GQLV (SEQ. ID. NO:1) to binding of the peptide comprising either the amino acid sequence ARRGQAV (SEQ. ID. NO: 4) or G(R/W)RFIRV (SEQ. ID. NO: 2) indicates a young heart or young areas of a heart vasculature. A disproportionately high ratio is greater than two, more preferably greater than three, and even more preferably greater than four. Alternatively, a disproportionately low ratio (i.e., ratio less than 2) indicates an old heart or old areas of a heart vasculature.

The order of administration of the peptides is not important in determining the condition of a heart. For example, the selective homing peptide comprising QA(Q/E)GQLV (SEQ. ID. NO: 1) conjugated to a detectable marker can be administered before, after, or simultaneously with the preferential homing peptide comprising the amino acid sequence ARRGQAV (SEQ. ID. NO: 4) or Q(R/W)RFIRV (SEQ. ID. NO: 2) conjugated to another detectable marker.

Furthermore, the homing peptides conjugated to a detectable marker can also be used to determine the prognosis of cardiac therapy. For example, an image obtained of a heart vasculature before therapy begins, which is indicative of its condition, can be compared to an image obtained after therapy begins. A decrease in the old areas of a heart vasculature or an increase in the young areas indicates an effective therapy.

In another embodiment, the functional moiety is a therapeutic agent. The therapeutic agent can be a small molecule or a biological molecule. A biological molecule is any molecule which contains a nucleic acid or amino acid sequence and has a molecular weight greater than 450.

Biological molecules which can be used as therapeutic agents include viral gene therapy vectors; viruses; nucleic acid molecules and oligonucleotides including antisense and dominant negative molecules; polypeptides, peptides, and proteins. Examples of proteins include microvasculature growth factors such as platelet derived growth factor, vascular endothelial growth factor, angiopoietin, and estrogen.

Small molecules include organic compounds, organometallic compounds, salts of organic and organometallic compounds, saccharides, amino acids, and nucleotides. Small molecules can further include molecules that would otherwise be considered biological molecules, except their molecular weight is not greater than 450. Thus, small molecules may be lipids, oligosaccharides, oligopeptides, and oligonucleotides, and their derivatives, having a molecular weight of 450 or less.

It is emphasized that small molecules can have any molecular weight. They are merely called small molecules because they typically have molecular weights less than 450. Small molecules include compounds that are found in nature as well as synthetic compounds.

In another embodiment, the invention provides methods for delivering a functional moiety to a heart which contain young areas or hearts. Functional moieties, such as detectable markers, can be delivered as described above. The function moiety can also be a therapeutic agent. The therapeutic agent can be used to treat young hearts or young areas of a heart in a cardiac pathology.

Therapeutic agents are targeted to young areas of a heart by administering an appropriate therapeutic agent conjugated to a peptide containing the amino acid sequence QA(Q/E)GQLV (SEQ. ID. NO: 1). Therefore, the therapeutic agent is selectively delivered to the appropriate areas with reduced adverse effects on other organs or areas of the heart.

For example, young areas or hearts can be treated in order to induce proliferation of the cells in the microvasculature of the heart. The proliferation of the young cells of the microvasculature in the heart can compensate for areas damaged by a cardiac pathology.

Therapeutic agents which are useful to treat young areas of a heart or young hearts are known to those in the art and include the therapeutic agents described herein. Therapeutic agents which induce proliferation of heart microvascular cells include, for example, growth factors, such as platelet derived growth factor, vascular endothelial growth factor, and angiopoietin.

In another embodiment, a functional moiety can be delivered to a heart containing old areas or hearts. Functional moieties, such as detectable markers, can be delivered as described herein. The function moiety can also be a therapeutic agent. The therapeutic agent can be used to treat old hearts or old areas of a heart in a cardiac pathology.

Therapeutic agents are targeted to the old area of a heart by administering an appropriate therapeutic agent conjugated to a peptide containing the amino acid sequence ARRGQAV (SEQ. ID. NO: 4) or G(R/W)RFIRV (SEQ. ID. NO: 2). Therefore, the therapeutic agent is preferentially delivered to areas damaged by a cardiac pathology.

Therapeutic agents which are useful to treat old areas of a heart in a particular cardiac disease are known to those in the art. The therapeutic agents include, for example, agents that inhibit apoptosis in old hearts or old areas of hearts. Such agents include, for example, estrogen.

Any cardiac pathology that results in damage to a heart can be treated in accordance with the present invention. Cardiac pathologies include, for example, myocardial infarction, myocardial hypertrophy, congenital heart disease, ischemic heart disease, and heart failure.

The conjugates are administered to a mammal in an effective amount. An "effective amount" is the amount of the conjugate that produces a desired effect. An effective amount will depend, for example, on the functional moiety conjugated to the homing peptide, the pathology being treated, and the age, size, and condition of the mammal. An effective amount of a particular conjugate for a particular cardiac pathology is known to, or can routinely be determined by, those skilled in the art.

The conjugate can be administered to a mammal by various routes, including, for example, orally, systemically, or parenterally, such as intravenously. The conjugate can be administered by injection or by intubation.

A mammal can be any mammal. Examples of mammals include primates, such as humans, laboratory animals, such as rats and mice, pet animals, such as dogs and cats, and farm animals, such as cows and sheep.

A conjugate is generally delivered as a pharmaceutical composition. The pharmaceutical composition can, for example, contain a pharmaceutically acceptable carrier. Such carriers are well known in the art and include, for example, aqueous solutions such as physiologically buffered saline or other solvents or vehicles such as glycols, glycerol, and oils such as olive oil.

A pharmaceutically acceptable carrier can contain physiologically acceptable compounds that act, for example, to stabilize or to increase the absorption of the complex. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art knows that the choice of a pharmaceutically acceptable carrier, including a physiologically acceptable compound, depends, for example, on the route of administration of the composition.

In another embodiment, mimics of peptides comprising amino acid sequences QA(Q/E)GQLV (SEQ. ID. NO: 1), ARRGQAV (SEQ. ID. NO: 4), or G(R/W)RFIRV (SEQ. ID. NO: 2) are discovered. A mimic is any compound having the same three-dimensional structure and binding property as peptides having amino acid sequence QA(Q/E)GQLV (SEQ. ID. NO: 1), ARRGQAV (SEQ. ID. NO: 4), or G(R/W)RFIRV (SEQ. ID. NO: 2).

The three-dimensional structure of a peptide can be determined by any known method in the art. Examples of methods for determining the three-dimensional structure of a peptide include, x-ray crystallography and computational methods, such as 3-D structure prediction programs based on, for example, homology modeling. Examples of such programs include SWISS-MODEL, which is available at http://www.expasy.ch/swissmod/SWISS-MODEL.html, and CPHmodels, which is available at http://www.cbs.dtu.dk/services/CPHmodels/.

Compounds comprising the three-dimensional structure of the homing peptides of the present invention can be identified by any known method in the art. Compounds can be identified by, for example, binding assays, competition assays, spectrophotometry, and x-ray crystallography. The compound can be a small molecule or a biological molecule. The selective and preferential homing capacity of the compounds can be determined as described above. Those compounds which selectively or preferentially home to TNF receptor(s) or BDNF receptor(s) in the vasculature of the heart are mimics.

The peptides of the invention and their mimics can act as an agonist or an antagonist depending on the ability or inability of the peptide or the mimic to activate the receptor. An agonist generally binds to a receptor and stimulates the function of the receptor. A peptide or mimic that activates TNF receptor(s) or BDNF receptor(s) is an agonist. Methods to determine whether a peptide or mimic activates TNF receptor(s) or BDNF receptor(s) are known to those skilled in the art.

An antagonist generally binds to a receptor and inhibits activation of the receptor. A peptide or mimic that inhibits the activation of TNF receptor(s) or BDNF receptor(s) is an antagonist. Method to determine whether a peptide or mimic inhibits the activation of TNF receptor(s) or BDNF receptor(s) are known to those skilled in the art.

An agonist can be useful, for example, in treating myocardial infarction of a young heart or young areas of a heart. Activation of TNF receptor(s) by the agonist can reduce the extent of myocardial damage to the heart.

In contrast, an antagonist can be used to inhibit the activation of TNF receptor(s), for example, to inhibit apoptosis of old hearts or old areas of a heart.

Similarly, an antagonist can be used to inhibit the activation of BDNF receptor(s) in old hearts of old areas of a heart, thereby preventing, for example, infiltration of inflammatory cells and aneurysm formation.

EXAMPLES

Example 1

ψY12 with Homology to TNFα Binds to Hearts in 3-Month Old Mice

Cardiac-homing phage clone ψY12 (SEQ ID NO: 10) containing the amino acid sequence QAQGQLV (SEQ ID NO: 1) (FIGS. 3A and 3B), which is homologous to TNFα (SEQ ID NO: 11), identified an aging-associated change in TNFα receptor pathways in the microvasculature of the older heart. In vivo injection of the ψY12 clone phage confirmed the diminished binding capacity of the TNFα-like phage in the older cardiac microvasculature (FIGS. 3C-3E), with only minimal binding in the subepicardium of aging hearts. Therefore, TNF receptor is altered in the microvasculature of the older heart.

Example 2

TNF Receptor Expression in Microvasculature of Young and Old Mice

Figure 4A:
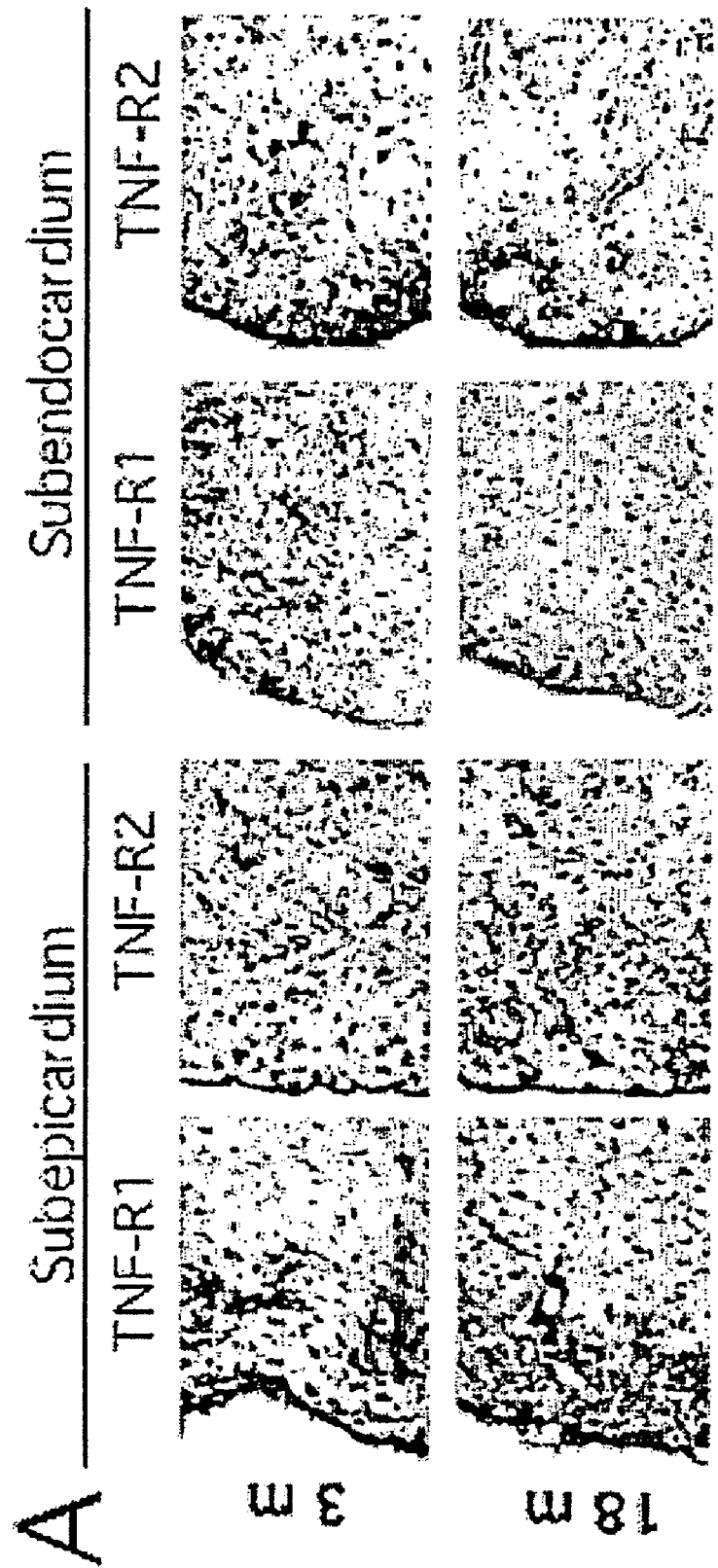
FIG. 4. Aging-associated alterations in cardiac microvascular TNFα receptor pathways. (A) Representative immunostaining for TNF receptor 1 and 2 in the subepicardium and subendocardium of 3- and 18-month old murine hearts. (B) TNF receptor 1 and 2 densities in the subendocardium of 3- and 18-month old murine hearts (n=3, each). (C) RT-PCR for PDGF-B induction after TNFα treatment of 4- and 24-month old rat CMECs.
Figures 4B, 4C:
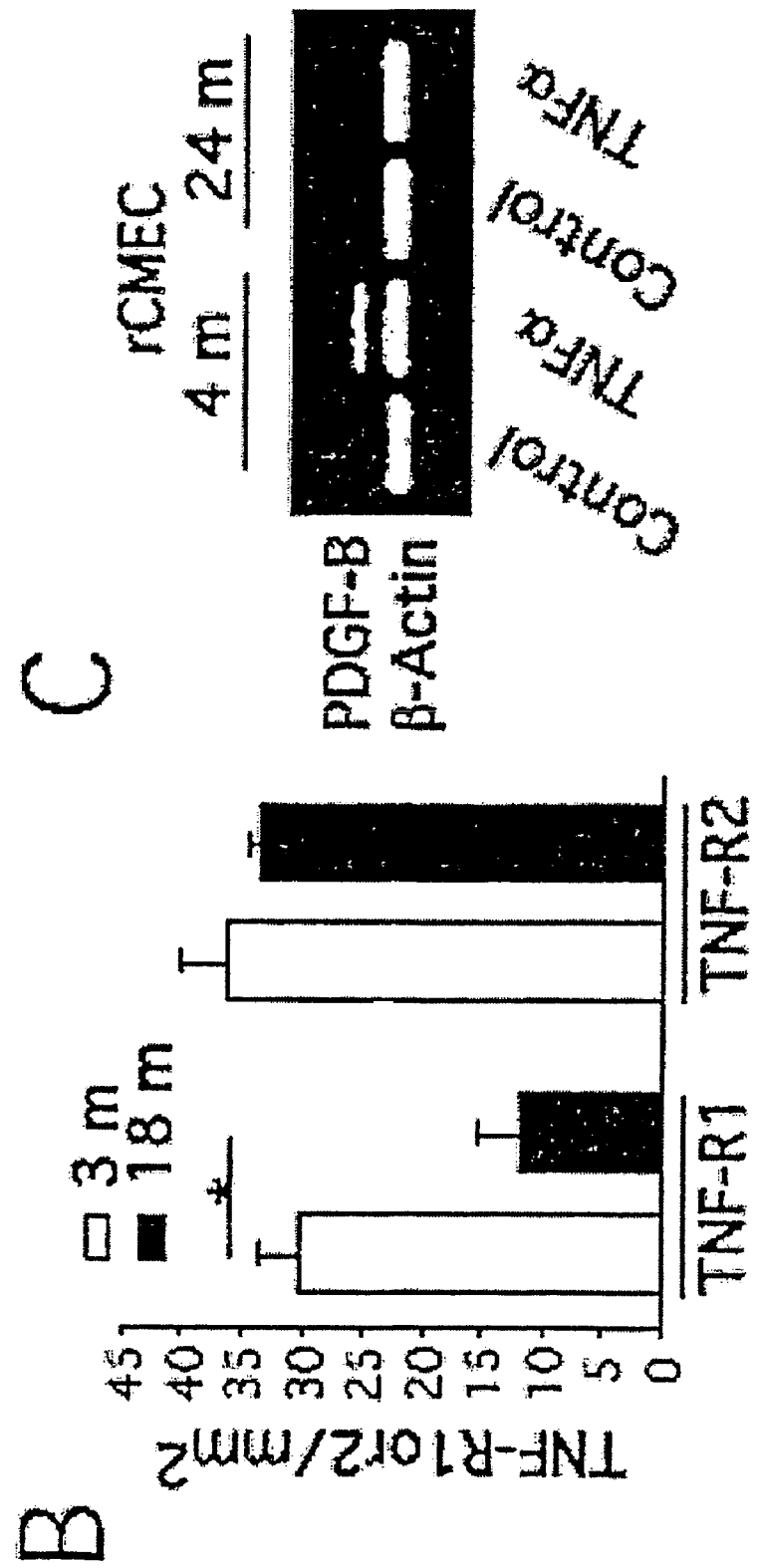

Immunostaining of 3- and 18-month old hearts revealed TNF receptor 2 in the microvasculature throughout the young and older hearts (FIGS. 4A and 4B). TNF receptor 1 was present in the microvasculature throughout the young hearts, however, in the older hearts, the receptor was restricted to the subepicardial microvasculature, consistent with the patterning of ψY12 in Example 1.

Example 3

Functional Significance of the Change in TNF Receptor in Aging Cardiac Microvasculature The functional significance of the changes in TNF receptor in the aging cardiac microvasculature was examined in vitro. Cardiac microvascular endothelial cells (CMECS) of 4 and 24-month old F344 rats were isolated and cultured. Briefly, the hearts were removed and minced in endothelial cell medium (DMEM containing 20% FBS, 1% endothelial cell growth factor, 1% endothelial cell growth supplement, 1% BME, $10^{-4}$% heparin and 1% penicillin [10,000 I.U./ml]/streptomycin [10,000 μg/ml]), and digested with medium containing 0.2% collagenase and 0.005% Dnase, and 5% FBS for 45 minutes with subsequent endothelial cells isolation by PECAM-mediated magnetic particle collection (Dynabeads). The resultant CMECs (Dil-LDL uptake>95%) were cultured for 2 passages and seeded into 12-well culture dish ($10^5$ cells/well) and grown to confluence. Medium was changed to serum free-DMEM for 1 hr and then to medium containing 2% FBS+TNFα (30 ng/ml) for 3 hr.

In vitro, TNFα induced platelet derived growth factor (PDGF)-B expression in cardiac microvascular endothelial cells (CMECs) from the young, but not in older hearts (FIG. 4C).

Example 4

In Vivo Response to TNFα

To examine the age-dependent effects of TNFα PDGF-B expression and protection from myocardial necrosis, sets of 4- and 24-month old F344 rats received intramyocardial injections of growth factor. Briefly, the rats were anesthetized and underwent left intercostals thoracotomy. After identifying the left anterior descending artery (LAD), 100 ng of TNFα in 50 μl PBS or PBS alone was injected through a 30 G needle using a 250 μl Hamilton syringe. Two injections (25 μl/injection 2 mm apart) were made at mid ventricular anterior wall. The chest wall was then closed, the lungs inflated, the rat extubated, and the tracheotomy closed.

Figure 5:
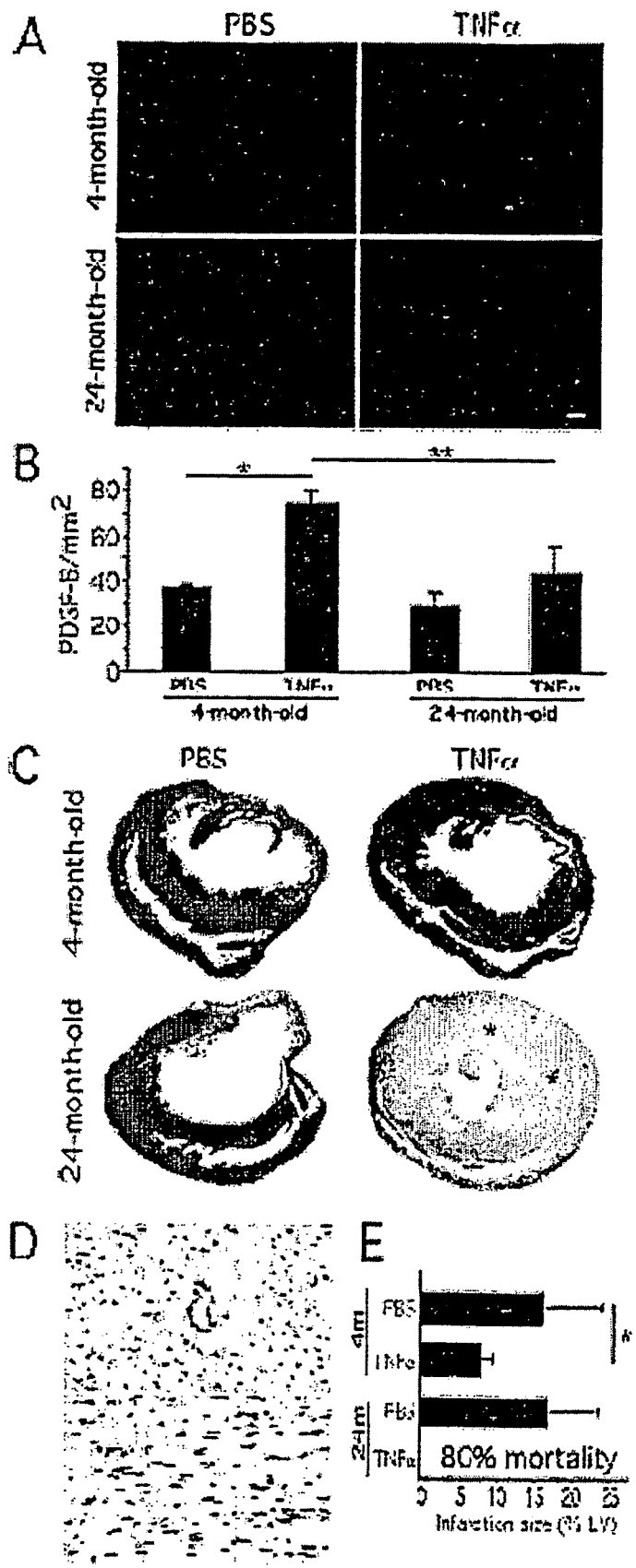
FIG. 5. Aging-associated alterations in TNFα cardioprotection. (A) Representative immunostaining for PDGF-B in rat hearts injected with TNFα or PBS vehicle 24 h prior to sacrifice. (B) Quantification of PDGF-B density in the injected hearts (n=3, each group). (C) Representative cardiac histology after coronary occlusion: Mason's trichrome staining for myocardial necrosis (14 day post-coronary occlusion) in 4- and 24-month old rat hears treated with PBS (4- and 24-month old, n=4 and 10, respectively) and TNFα (4-month old, n=4); and (D) tunnel staining for apoptosis (DAB) with hematoxylin counter stain (2 day post-coronary occlusion) in 24-month old hearts treated with TNFα (n=10; 80% mortality vs. PBS 0%; p<0.05). (E) Quantification of myocardial necrosis in rat hearts 14 day post-coronary occlusion.

In vivo, TNFα specifically induced increase of PDGF-B in the young hearts, while having minimal effect on the aging tissue (FIGS. 5A and 5B). Moreover, TNFα markedly reduced the extent of myocardial infarction in the young hearts (FIGS. 5C and 5D). In the older rats TNFα was harmful, inducing extensive apoptosis in the anterior left ventricular wall and resulting in an 80% mortality within 72 h of coronary occlusion.

Example 5

ψO40 with Homology to BDNF Binds to Heart in Older Mice

Figure 6:
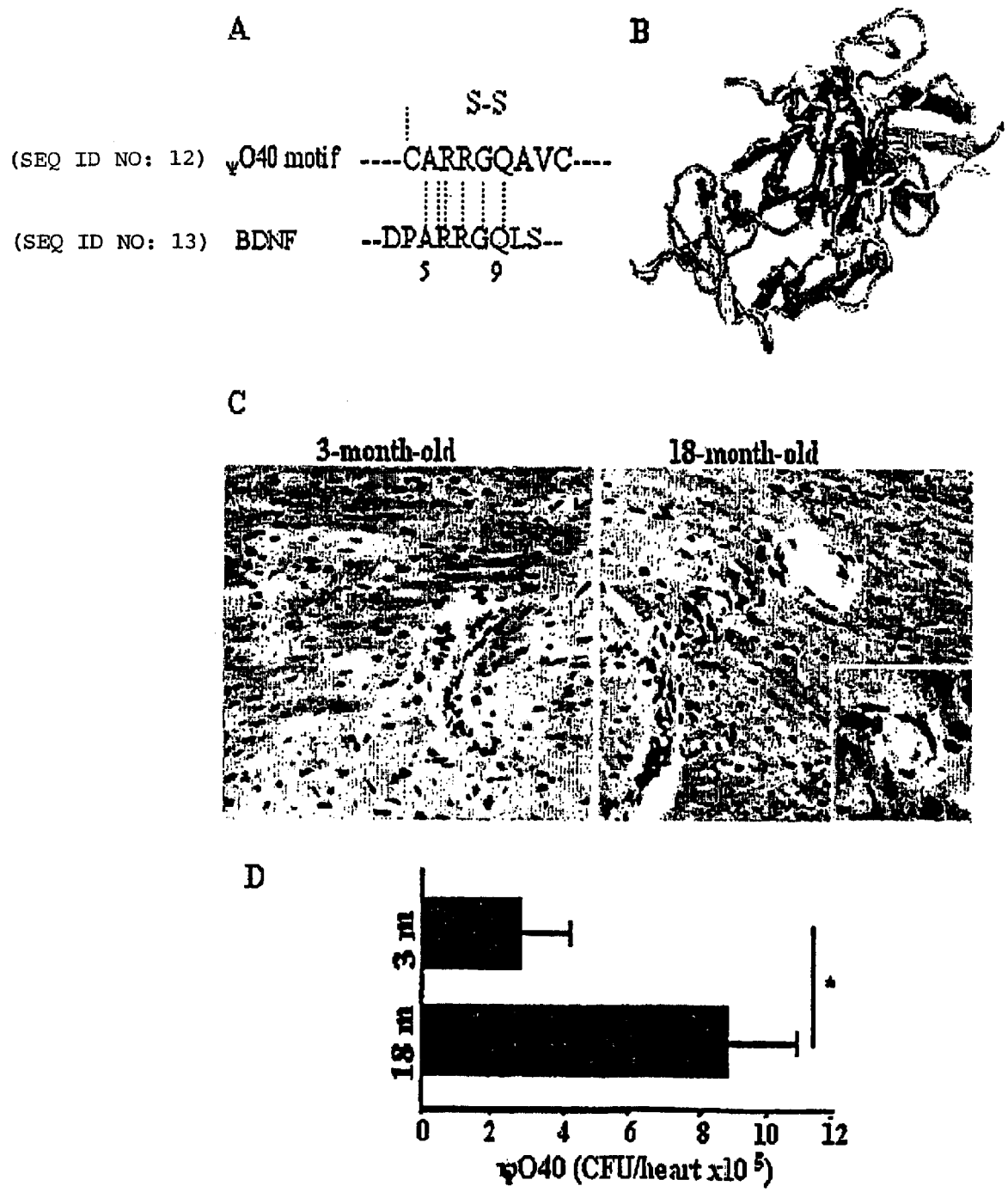
FIG. 6. Identification of aging-associated changes in BDNF homologous phage cardiac microvascular epitope binding. (A) ψO40 epitope sequence homology to BDNF. (B) Homologous region is highlighted yellow in the 3-D structure of BDNF. (C) Representative phage immunostaining patterns in hearts with isolated ψO40 clones with phage binding the cardiac microvasculature of 18-month-old hearts with minimal binding to 3-month-old hearts (n=3, each). (D) ψO40 phage titers of 3- and 18-month-old hearts (n=3, each). *P<0.05 3-vs. 18-month-old hearts.
Figure 7:
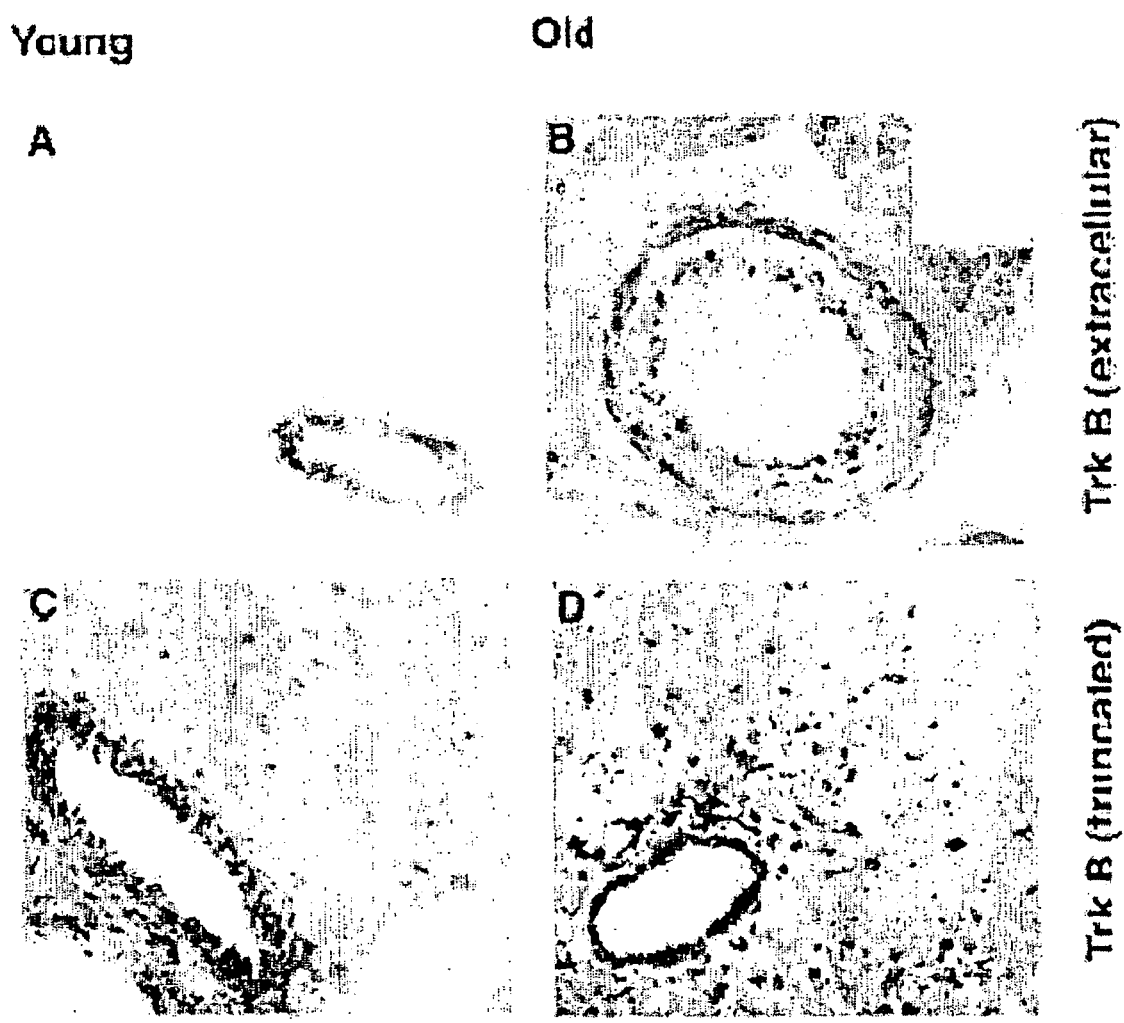
FIG. 7A-D. Aging associated alterations in cardiac microvascular BDNF receptor pathways, immunostaining for the full-length receptor as well as the truncated trkB receptor in sections of 3- and 18-month old rat heats.

Cardiac-homing phage clone ψO40 (SEQ ID NO: 12) containing the amino acid sequence ARRGQAV (SEQ ID NO: 4), which is partially homologous to BDNF (SEQ ID NO: 13) (FIGS. 6A and 6B), identified an aging-associated change in BDNF receptor pathways in the microvasculature of the older heart. In vivo injection of the ψO40 clone phage combining with immunostaining and recovered ψO40 phage CFU assay confirmed the more binding capacity of the BDNF-homologous phage in the older cardiac microvasculature while only minimal binding of the subepicardium of the young hearts, suggesting that BDNF receptor(s) may be altered in the microvasculature of the older hearts (FIGS. 6C and 6D).

Indeed, immunostaining of the BDNF receptor, trkB, demonstrated that the density of the truncated trkB$^{trk}$ receptor was significantly greater in the hearts of older mice and rats compared with the hearts of younger mice and rats, while the distribution of the full-length receptor was similar in both age groups (FIG. 7A-D).

Example 6

Functional Significance of the Change in BDNF Receptor in Aging Cardiac Microvasculature To probe the age-dependent effects of BDNF on the aging heart, sets of 4- and 24-month old F344 rats (n=3, each set) received intramyocardial injections of the growth factor as described in Edelberg et al. (*Circul* 2002, 105:608-613). Briefly, the rats were anesthetized and underwent left intercostals thoracotomy. After the left anterior descending artery (LAD) was identified, 1 µg of rhBDNF (R&D Systems, 248BS005) in 50 µl of PBS or PBS alone was injected through a 30 G needle using a 250 µl Hamilton syringe. Two injections (25 µl/injection 2 mm apart) were made at mid-left ventricular anterior wall. The chest wall was then closed, the lungs inflated, the rat extubated, and the tracheotomy closed.

Rats receiving pretreatment alone (BDNF or control) were sacrificed 24 hr postinjection. The hearts were excised, fixed, sectioned, immunostained for ED1 and ED2, and visualized with DAB. Staining was quantified in the anterior and posterior left ventricular wall at the level of the mid-papillary muscles from each heart, as described in Edelberg et al. (*Circul*. 2002, 105:608-613) [ten high power fields (40× per heart]. Two investigators performed quantification independently in a blinded fashion.

Figure 8:
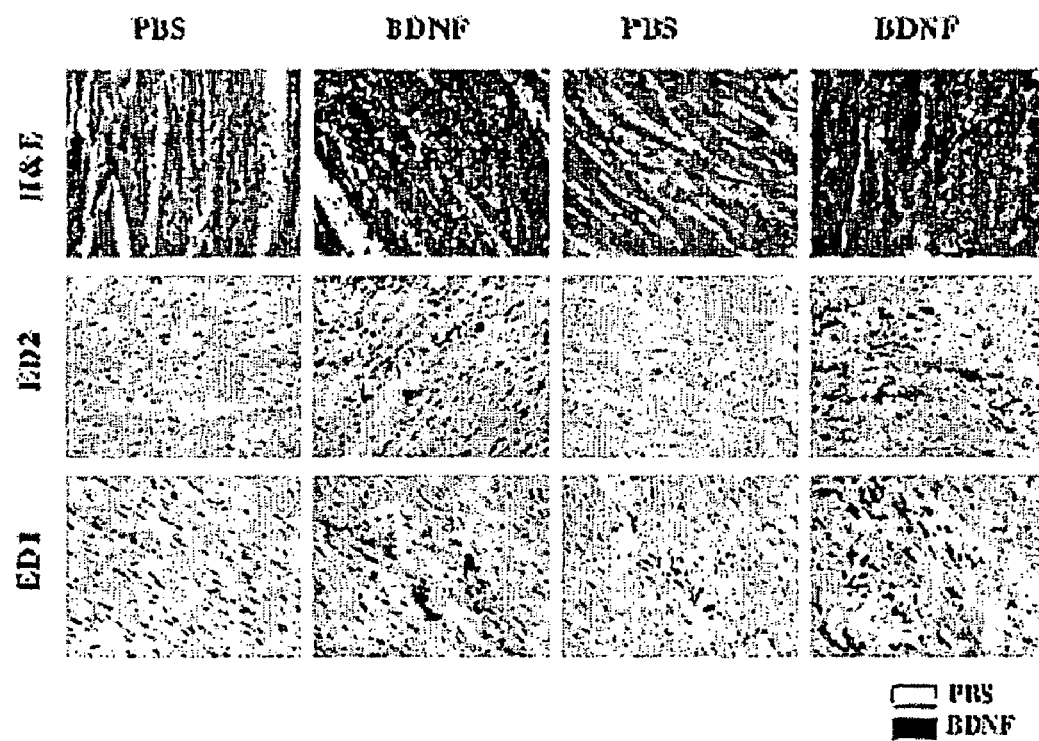
FIG. 8. BDNF induction of activated macrophage recruitment in the hearts of old but not young rats. (A) Representative histology and immunostains for ED2 and ED1 in 4- and 24-month-old rat hearts injected with BDNF or PBS 24 hr prior to tissue harvest. (B) Quantification of ED1 and ED2 cellular density in the injected hearts (n=3, each group). *P<0.05 BDNF vs. PBS.
Figure 8:
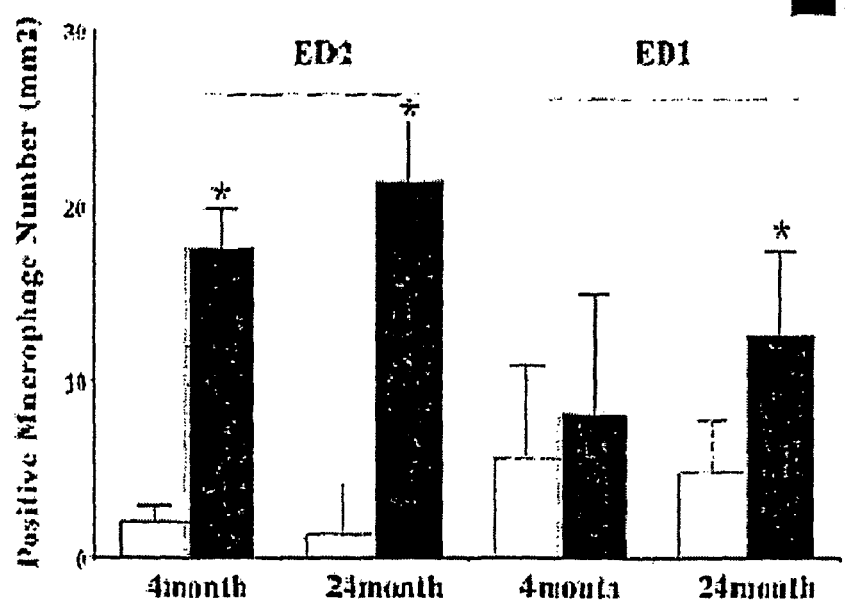

The functional significance of the alteration in BDNF receptor pathway in the aging cardiac microvaculature was examined in vivo. Intramyocardail injection of BDNF 24 hr prior to sacrifice resulted in a similar infiltration of macrophage in both young and older rat hearts, as evidenced by histology and immunostaining for ED2, FIG. 8. However, in the older heart BDNF-mediated induction of activated/inflammatory macrophage was significantly greater compared with young hearts, as evidences by immunostaining for ED1.

Example 7

In Vivo Response to BDNF in Young and Old Myocardial Infarction Hearts

The potential effects of BDNF pretreatments were studied in a myocardial infarction model. One day after intramyocarial injection of BDNF (4-month old, n=5; 24-month old, n=5) or control (4-month old, n=5; 24-month old, n=5), the rats were anesthetized, the heart exposed, and the LAD ligated just below (4-month old) or 2 mm below (24-month old, to produce a similar size myocardial infarction to the younger rats) the left atrial appendage with 8-0 nylon sutures. Pallor and regional wall motion abnormality of the left ventricle confirmed occlusion. The chest wall was closed and, after recovery, the rats were returned to the animal facility for 14 d. At the termination of the experiment, the rats were sacrificed and the hearts explanted. The extent of myocardial infarction measured at the level of the mid-papillary heart muscles was scored by Masson's trichrome staining, and the images were analyzed in a blinded fashion employing ImageJ 1.22 software (NIH Image). Infarction size was expressed as a percentage of the total left ventricle myocardial area. Differences were tested for statistical significance by the Wilcoxon rank-sum test. P value<0.05 was considered significant.

Figure 9A:
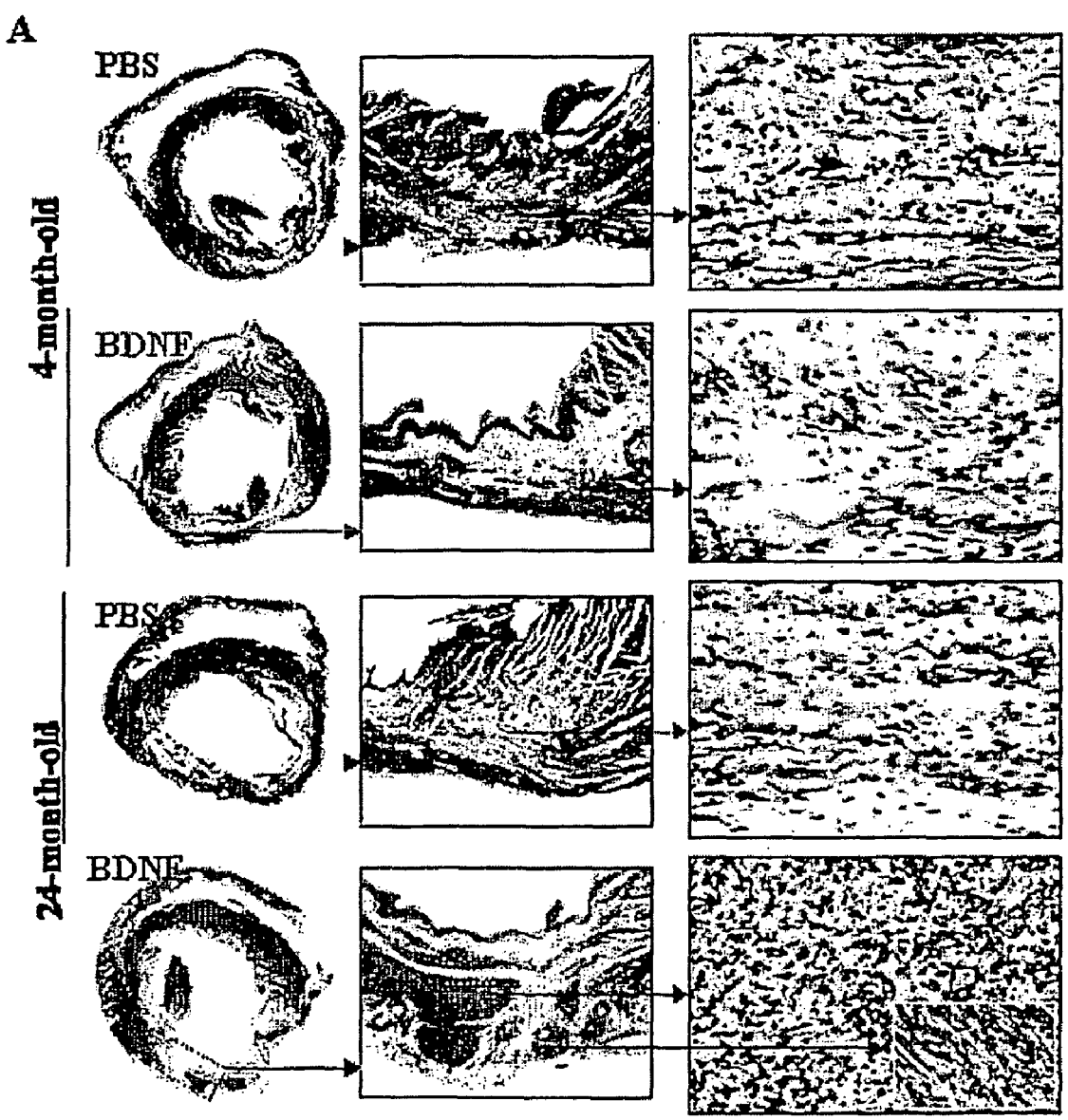
FIG. 9. Aging-associated alterations in BDNF cardiac actions. (A) Representative cardiac histology after coronary occlusion: Masson's trichrome staining for myocardial necrosis (14 d post-coronary occlusion) in 4- and 24-month-old rat hearts treated with PBS and BDNF. (B) Quantification of myocardial necrosis in rat hearts 14 d post-coronary occlusion.
Figure 9B:
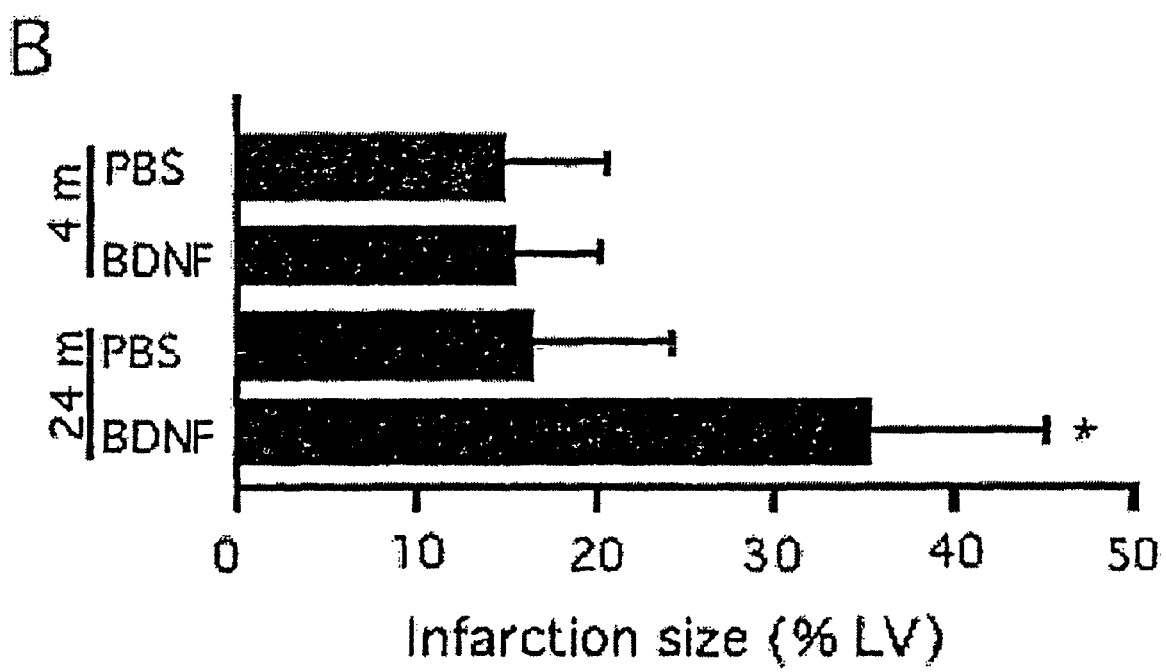
Figure 10:
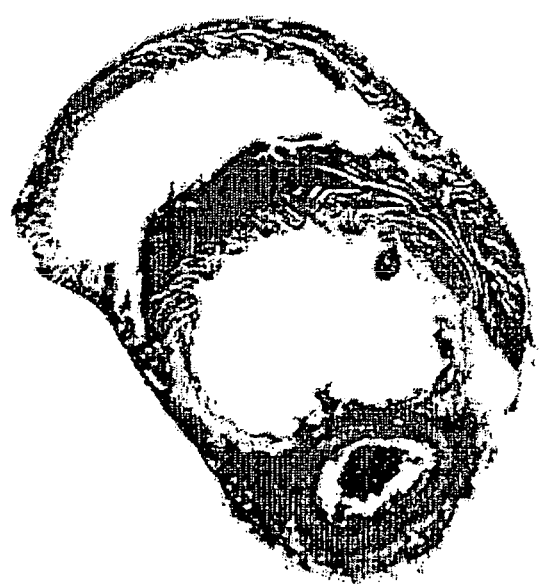
FIG. 10. Aging-associated BDNF cardiac aneurysm formation post coronary occlusion. (A) Representative cardiac histology (Masson's trichrome) cardiac aneurysm formed in 3/5 18-month-old rats receiving intramyocardial injection of BDNF 1 d prior to coronary occlusion. (B) Inflammatory infiltrate in BDNF injected heart.
Figure 10:
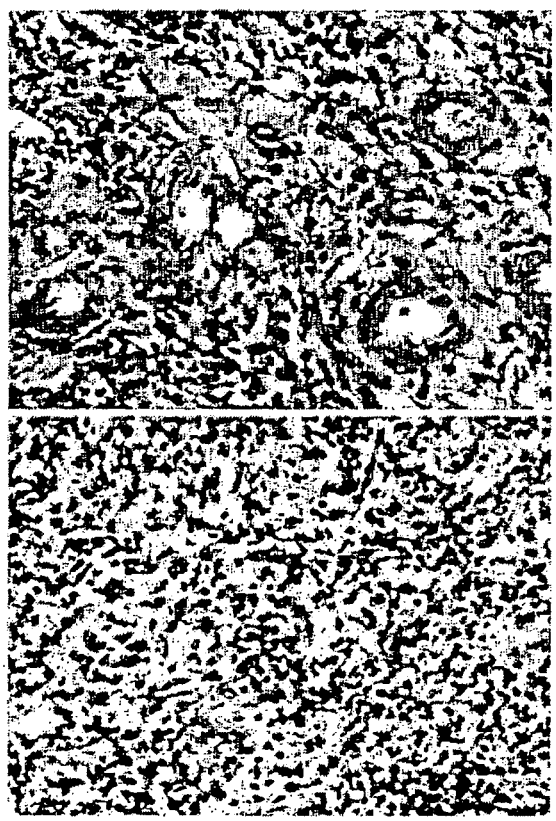

In myocardial infarction studies, BDNF demonstrated a similar age-associated effect on cardiac physiology. In the young heart, intramyocardial injection of BDNF 24 hr before coronary occlusion did not alter myocardial infarction size compared with PBS controls (FIG. 9). In the older rats, BDNF was deleterious, with significantly more extensive myocardial infarctions compared with hearts injected with control. Moreover, BDNF injection resulted in the formation of ventricular wall aneurysms (3/5 rats) with persistent macrophage infiltrates two weeks after coronary occlusion (FIG. 10).

INCORPORATION OF SEQUENCE LISTING

Incorporated herein by reference in its entirety is the Sequence Listing for the application. The Sequence Listing is disclosed on a computer-readable ASCII text file titled, "sequence_listing2.txt", created on Jan. 5, 2011. The sequence.txt file is 4.74 kb in size.

---

What is claimed is:

1. A method for delivering a functional moiety to a trkB receptor in the heart microvasculature in a mammal, the method comprising administering a conjugate, said conjugate comprising a peptide comprising the amino acid sequence of SEQ ID NO: 4 and said functional moiety.

2. A method according to claim 1, wherein said functional moiety is a therapeutic agent.

3. A method according to claim 2, wherein said therapeutic agent is estrogen.

4. A method according to claim 1, wherein said functional moiety is a detectable marker.

* * * * *

SEQUENCE LISTING

<160> NUMBER OF SEQ ID NOS: 13

<210> SEQ ID NO 1
<211> LENGTH: 7
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (3)..(3)
<223> OTHER INFORMATION: X is Q or E

<400> SEQUENCE: 1

Gln Ala Xaa Gly Gln Leu Val
1               5

<210> SEQ ID NO 2
<211> LENGTH: 7
<212> TYPE: PRT
<213> ORGANISM: Artificial sequence
<220> FEATURE:
<223> OTHER INFORMATION: Synthetic sequence

```
<220> FEATURE:
<221> NAME/KEY: MISC_FEATURE
<222> LOCATION: (2)..(2)
<223> OTHER INFORMATION: X is R or W

<400> SEQUENCE: 2

Gly Xaa Arg Phe Ile Arg Val
1               5

<210> SEQ ID NO 3
<211> LENGTH: 7
<212> TYPE: PRT
<213> ORGANISM: Artificial sequence
<220> FEATURE:
<223> OTHER INFORMATION: Synthetic sequence

<400> SEQUENCE: 3

Gln Ala Gln Gly Gln Leu Val
1               5

<210> SEQ ID NO 4
<211> LENGTH: 7
<212> TYPE: PRT
<213> ORGANISM: Artificial sequence
<220> FEATURE:
<223> OTHER INFORMATION: Synthetic sequence

<400> SEQUENCE: 4

Ala Arg Arg Gly Gln Ala Val
1               5

<210> SEQ ID NO 5
<211> LENGTH: 7
<212> TYPE: PRT
<213> ORGANISM: Artificial sequence
<220> FEATURE:
<223> OTHER INFORMATION: Synthetic sequence

<400> SEQUENCE: 5

Gly Arg Arg Phe Ile Arg Val
1               5

<210> SEQ ID NO 6
<211> LENGTH: 152
<212> TYPE: PRT
<213> ORGANISM: Homo sapiens

<400> SEQUENCE: 6

Arg Thr Pro Ser Asp Lys Pro Val Ala His Val Ala Asn Pro Gln
1               5                   10                  15

Ala Glu Gly Gln Leu Gln Trp Leu Asn Arg Arg Ala Asn Ala Leu Leu
            20                  25                  30

Ala Asn Gly Val Glu Leu Arg Asp Asn Gln Leu Val Val Pro Ser Glu
        35                  40                  45

Gly Leu Tyr Leu Ile Tyr Ser Gln Val Leu Phe Lys Gly Gln Gly Cys
    50                  55                  60

Pro Ser Thr His Val Leu Leu Thr His Thr Ile Ser Arg Ile Ala Val
65                  70                  75                  80

Ser Tyr Gln Thr Lys Val Asn Leu Leu Ser Ala Ile Lys Ser Pro Cys
                85                  90                  95

Gln Arg Glu Thr Pro Glu Gly Ala Glu Ala Lys Pro Trp Tyr Glu Pro
            100                 105                 110

Ile Tyr Leu Gly Gly Val Phe Gln Leu Glu Lys Gly Asp Arg Leu Ser
        115                 120                 125
```

```
Ala Glu Ile Asn Arg Pro Asp Tyr Leu Leu Phe Ala Glu Ser Gly Gln
        130                 135                 140

Val Tyr Phe Gly Ile Ile Ala Leu
145                 150

<210> SEQ ID NO 7
<211> LENGTH: 119
<212> TYPE: PRT
<213> ORGANISM: Homo sapiens

<400> SEQUENCE: 7

His Ser Asp Pro Ala Arg Arg Gly Gln Leu Ser Val Cys Asp Ser Ile
1               5                   10                  15

Ser Glu Trp Val Thr Ala Ala Asp Lys Lys Thr Ala Val Asp Met Ser
            20                  25                  30

Gly Gly Thr Val Thr Val Leu Glu Lys Val Pro Val Ser Lys Gly Gln
        35                  40                  45

Leu Lys Gln Tyr Phe Tyr Glu Thr Lys Cys Asn Pro Met Gly Tyr Thr
    50                  55                  60

Lys Glu Gly Cys Arg Gly Ile Asp Lys Arg His Trp Asn Ser Gln Cys
65                  70                  75                  80

Arg Thr Thr Gln Ser Tyr Val Arg Ala Leu Thr Met Asp Ser Lys Lys
                85                  90                  95

Arg Ile Gly Trp Arg Phe Ile Arg Ile Asp Thr Ser Cys Val Cys Thr
            100                 105                 110

Leu Thr Ile Lys Arg Gly Arg
        115

<210> SEQ ID NO 8
<211> LENGTH: 7
<212> TYPE: PRT
<213> ORGANISM: Artificial sequence
<220> FEATURE:
<223> OTHER INFORMATION: Synthetic sequence

<400> SEQUENCE: 8

Gln Ala Glu Gly Gln Leu Val
1               5

<210> SEQ ID NO 9
<211> LENGTH: 7
<212> TYPE: PRT
<213> ORGANISM: Artificial sequence
<220> FEATURE:
<223> OTHER INFORMATION: Synthetic sequence

<400> SEQUENCE: 9

Gly Trp Arg Phe Ile Arg Val
1               5

<210> SEQ ID NO 10
<211> LENGTH: 9
<212> TYPE: PRT
<213> ORGANISM: Artificial sequence
<220> FEATURE:
<223> OTHER INFORMATION: Synthetic sequence

<400> SEQUENCE: 10

Cys Gln Ala Gln Gly Gln Leu Val Cys
1               5

<210> SEQ ID NO 11
```

-continued

```
<211> LENGTH: 10
<212> TYPE: PRT
<213> ORGANISM: Artificial sequence
<220> FEATURE:
<223> OTHER INFORMATION: Synthetic sequence

<400> SEQUENCE: 11

Asn Pro Gln Ala Glu Gly Gln Leu Gln Val
1               5                   10

<210> SEQ ID NO 12
<211> LENGTH: 9
<212> TYPE: PRT
<213> ORGANISM: Artificial sequence
<220> FEATURE:
<223> OTHER INFORMATION: Synthetic sequence

<400> SEQUENCE: 12

Cys Ala Arg Arg Gly Gln Ala Val Cys
1               5

<210> SEQ ID NO 13
<211> LENGTH: 9
<212> TYPE: PRT
<213> ORGANISM: Artificial sequence
<220> FEATURE:
<223> OTHER INFORMATION: Synthetic sequence

<400> SEQUENCE: 13

Asp Pro Ala Arg Arg Gly Gln Leu Ser
1               5
```